(12) United States Patent
McGuinness et al.

(10) Patent No.: US 10,464,066 B2
(45) Date of Patent: Nov. 5, 2019

(54) DIAGNOSTIC CHIP

(71) Applicant: Hewlett-Packard Development Company, L.P., Houston, TX (US)

(72) Inventors: Nicholas McGuinness, San Diego, CA (US); Chantelle M. Domingue, Corvallis, OR (US); Jeremy Sells, Corvallis, OR (US); Manish Giri, Corvallis, OR (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 121 days.

(21) Appl. No.: 15/546,565

(22) PCT Filed: Jan. 30, 2015

(86) PCT No.: PCT/US2015/013708
§ 371 (c)(1),
(2) Date: Jul. 26, 2017

(87) PCT Pub. No.: WO2016/122572
PCT Pub. Date: Aug. 4, 2016

(65) Prior Publication Data
US 2018/0008983 A1 Jan. 11, 2018

(51) Int. Cl.
*B01L 3/00* (2006.01)
*G01N 15/02* (2006.01)
(Continued)

(52) U.S. Cl.
CPC ..... *B01L 3/502761* (2013.01); *B01L 3/50273* (2013.01); *G01N 15/0272* (2013.01);
(Continued)

(58) Field of Classification Search
CPC ......... B60L 3/502773; B60L 3/502761; B60L 3/5027; B60L 3/502; B60L 3/50; B60L 3/00
(Continued)

(56) References Cited

U.S. PATENT DOCUMENTS

2007/0003434 A1* 1/2007 Padmanabhan ..... B01L 3/50273
422/400
2007/0099290 A1 5/2007 Iida et al.
(Continued)

FOREIGN PATENT DOCUMENTS

| CN | 102879377 | 1/2013 |
| WO | WO-2008036083 | 3/2008 |
| WO | WO-2014178827 | 11/2014 |

OTHER PUBLICATIONS

Herold et al.; Lab-on-a-chip Technology (vol. 2): Biomolecular Separation and Analysis; Aug. 2009: http://www.horizonpress.com/loc2.
(Continued)

*Primary Examiner* — Christine T Mui
(74) *Attorney, Agent, or Firm* — Fabian VanCott (57) ABSTRACT

A microfluidic diagnostic chip may comprise a main fluid channel comprising a main pump, a secondary fluid channel branching off from the main fluid channel, and a secondary pump within the secondary fluid channel wherein the secondary pump is to pull a particle of analyte of a first size from a fluid passing through the main channel, the fluid comprising particles of analyte of the first size and of a number of larger sizes. A method of analyzing an analyte on a microfluidic chip may comprise pumping, with a main microfluidic pump, a fluid comprising an analyte particle through a main microfluidic channel fluidly coupled to a fluid slot and sorting the analyte particle within the fluid through a secondary microfluidic channel by pulling the
(Continued)

analyte particle into the secondary microfluidic channel with a secondary microfluidic pump.

20 Claims, 6 Drawing Sheets

(51) Int. Cl.
  *G01N 15/10* (2006.01)
  *G01N 15/00* (2006.01)
(52) U.S. Cl.
  CPC ..... *G01N 15/1031* (2013.01); *G01N 15/1056* (2013.01); *B01L 2200/0652* (2013.01); *B01L 2300/0627* (2013.01); *B01L 2300/0816* (2013.01); *B01L 2300/0864* (2013.01); *B01L 2400/0439* (2013.01); *B01L 2400/0442* (2013.01); *B01L 2400/0487* (2013.01); *G01N 2015/0065* (2013.01); *G01N 2015/0288* (2013.01); *G01N 2015/1006* (2013.01); *G01N 2015/1062* (2013.01); *G01N 2015/1081* (2013.01); *G01N 2015/1087* (2013.01)
(58) Field of Classification Search
  USPC .......................................... 422/502, 500, 50
  See application file for complete search history.

(56) References Cited

U.S. PATENT DOCUMENTS

| | | |
|---|---|---|
| 2008/0194012 A1 | 8/2008 | Lee et al. |
| 2009/0283456 A1 | 11/2009 | Le Vot et al. |
| 2011/0089328 A1 | 4/2011 | Li |
| 2011/0151500 A1* | 6/2011 | Hosokawa ......... G01N 33/4905 435/29 |
| 2011/0312646 A1 | 12/2011 | Silverbrook et al. |
| 2012/0135396 A1 | 5/2012 | McDevitt et al. |
| 2012/0149021 A1 | 6/2012 | Yung et al. |
| 2012/0301867 A1 | 11/2012 | Kumo et al. |
| 2013/0036793 A1 | 2/2013 | White et al. |
| 2013/0330708 A1 | 12/2013 | Huang et al. |
| 2014/0220673 A1 | 8/2014 | Chiu et al. |
| 2014/0305196 A1 | 10/2014 | Ellis et al. |
| 2014/0377145 A1 | 12/2014 | Govyadinov et al. |
| 2014/0378352 A1 | 12/2014 | Daridon |

OTHER PUBLICATIONS

International Search Report, Korean Intellectual Property Office, dated Sep. 24, 2015, Hewlett-Packard Development Company. L.P., PCT Application No. PCT/US2015/013708 3 pages.

McGuinness et al., Microfluidic Sensing Device, Appln. No. PCT/US2014/0137848; Filed Jan. 30, 2014.

* cited by examiner

DIAGNOSTIC CHIP

BACKGROUND

Infectious diseases and other medical conditions affect human life on a continual basis. Developments have been made to detect the presence of, for example, antigens in blood or other fluids in order to diagnose a patient's illness. In some cases, a microfluidic device is used to analyze an analyte.

BRIEF DESCRIPTION OF THE DRAWINGS

The accompanying drawings illustrate various examples of the principles described herein and are a part of the specification. The illustrated examples are given merely for illustration, and do not limit the scope of the claims.

DETAILED DESCRIPTION

As mentioned above, a microfluidic device such as a microfluidic diagnostic chip (MDC) receives a fluid including an analyte and detects pathogens or other anomalies within the fluid. An alternative to implementing an MDC would be to take a sample of a fluid including an analyte from and transfer that sample to a lab for analysis. This analysis process requires an operator performing a series of precise steps with sensitive and expensive reagents in order to properly process the sample. The person running the test usually has been specifically trained to conduct the analysis.

In one specific analysis of a fluid including an analyte, the process may include counting a number of particles in the fluid including the analyte particle. In one example, the particles may include human blood cells as the analyte and the count of those cells may help further a diagnosis of a patient. An MDC that counts cells may still require a trained professional to mix the analyte and reagents before introducing the fluid into the MDC. Even if this mixture is correctly prepared, the MDC may still fail to properly count the number of cells due to the fact that any given fluid (i.e. blood) comprises more than one type of cell or particle and the MDC cannot distinguish between the two types.

The present specification, therefore, describes in one example a microfluidic diagnostic chip comprising a main fluid channel comprising a main pump, a secondary fluid channel branching off from the main fluid channel, and a secondary pump within the secondary fluid channel wherein the secondary pump is to pull a particle of analyte of a first size from a fluid passing through the main channel, the fluid comprising particles of analyte of the first size and of a number of larger sizes. As a result, an untrained person may add a fluid comprising an analyte to the MDC and get a relatively more accurate result and diagnosis.

The present specification further describes in another example a diagnostic chip comprising a first fluid channel comprising a first sensor to be communicatively coupled to a particle differential module and a second fluid channel leading off from the first fluid channel, the second fluid channel having a smaller diameter than the first fluid channel, the second fluid channel comprising a second sensor to be communicatively coupled to the particle differential module wherein the particle differential module is to compares a number of analyte particles within a fluid that have passed through the first fluid channel to a number of analyte particles of the fluid that have that have been pulled through the second fluid channel using a first micropump.

The present specification also describes, in yet another examples a method of analyzing an analyte on a microfluidic diagnostic chip comprising pumping, with a main microfluidic pump, a fluid comprising an analyte particle through a main microfluidic channel fluidly coupled to a fluid slot and sorting the analyte particle within the fluid through a secondary microfluidic channel by pulling the analyte particle into the secondary microfluidic channel with a secondary microfluidic pump.

In the present specification and in the appended claims, the term "fluid" is meant to be understood broadly as any substance that continually deforms (flows) under an applied shear stress. In one example, a fluid includes an analyte. In another example, a fluid includes a reagent or reactant. In another example, a fluid includes an analyte and a reagent or reactant. In still another example, a fluid includes an analyte, a reagent or reactant, among others.

Additionally, in the present specification and in the appended claims the term "analyte" is meant to be understood as any substance within a fluid that may be placed in a microfluidic diagnostic chip (MDC) to be analyzed. In one example, the analyte may be any constituent substance within a fluid such as, but not limited to, animal or human blood, animal or human urine, animal or human feces, animal or human mucus, animal or human saliva, or yeast, among others. In one example, the analyte may be a number of particles within the fluid such as a blood cell. In this example, a specific type of blood cell is an analyte because it is to be analyzed by the MDC.

Further, in the present specification and in the appended claims the term "pathogen" is meant to be understood as any substance that can produce a disease. In one example, the pathogen may be found in any fluid as described above.

Still further, in the present specification and in the appended claims the term "reagent" is meant to be understood as a substance or compound that is added to a system in order to bring about a chemical reaction, or added to see if a reaction occurs. A reactant is meant to be understood as a substance that is consumed in the course of a chemical reaction. In one example, the reagent may be included within a fluid.

Even still further, as used in the present specification and in the appended claims, the term "a number of" or similar language is meant to be understood broadly as any positive number comprising 1 to infinity; zero not being a number, but the absence of a number.

In the following description, for purposes of explanation, numerous specific details are set forth in order to provide a thorough understanding of the present systems and methods. It will be apparent, however, to one skilled in the art that the present apparatus, systems and methods may be practiced without these specific details. Reference in the specification to "an example" or similar language means that a particular feature, structure, or characteristic described in connection with that example is included as described, but may not be included in other examples.

Figure 1:
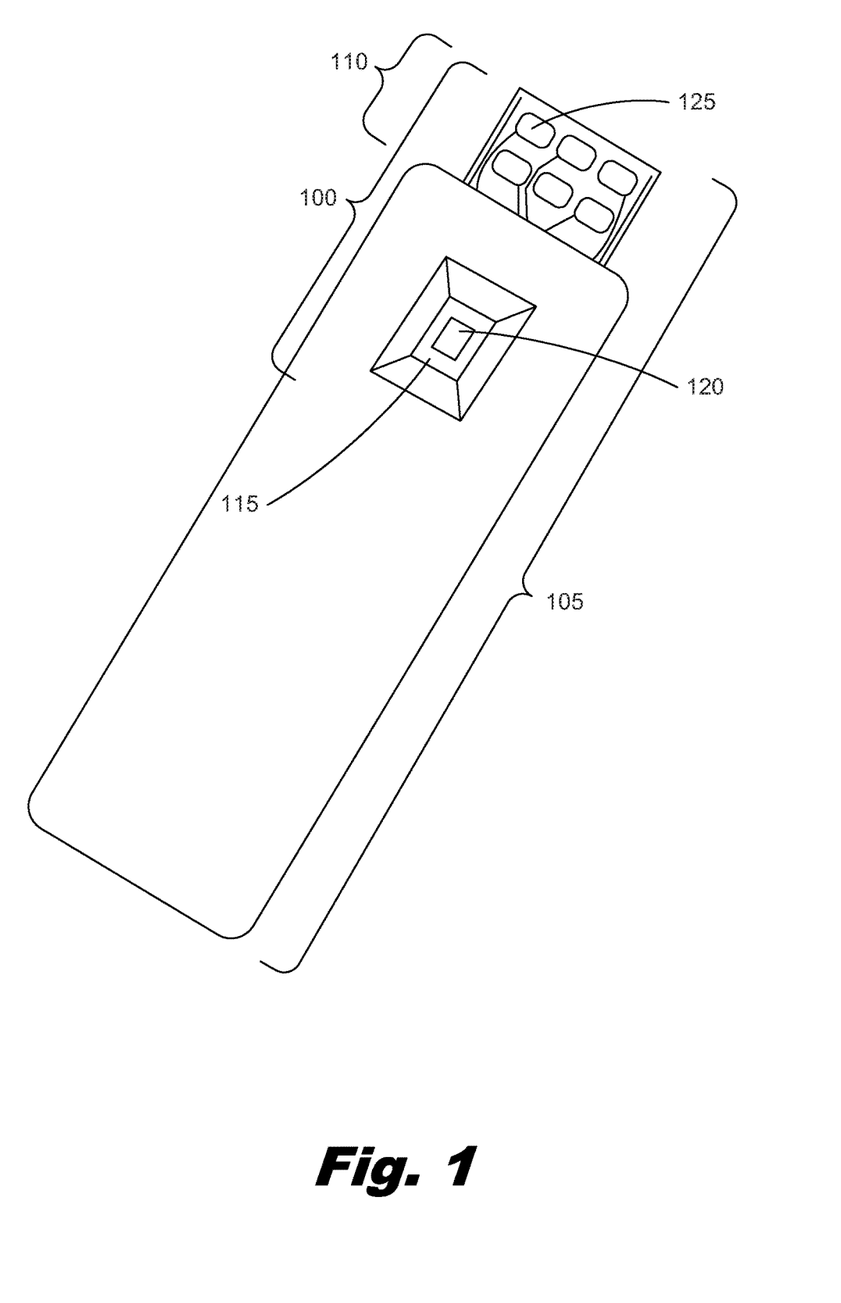
FIG. 1 is a diagram of a microfluidic diagnostic chip incorporated into a cassette for analyzing an analyte according to one example of the principles described herein.

Turning now to the figures, FIG. 1 is a diagram of a microfluidic diagnostic chip (100) incorporated into a cassette (105) for analyzing an analyte according to one example of the principles described herein. In the example shown in FIG. 1, the MDC (100) is part of a cassette. The cassette (105) further includes an electronic device interface (110) electrically coupled to the MDC (100). In one example, the MDC (100) may be 1 to 30 mm long and 2 to 5 mm wide. In another example, the width of the MDC (100) is approximately 2 mm wide. In one example, the MDC (100) may comprise a silicon substrate onto which a number of electrical lines, cavities, pumps and sensors may be defined and created.

The electronic device interface (110) may allow the MDC (100) to receive instructions and power from an external source such as a computing device. In this example, the MDC (100) is the part of the cassette (105) that receives a fluid including an analyte while the cassette (105) and electronic device interface (110) provide the physical body to house the MDC and the power and instructions to operate the MDC (100) respectively.

The cassette (105) may serve as a housing into which the MDC (100) and electronic device interface (110) are housed and protected from contamination and damage. The cassette (105) may also serve as a structure onto which a user may apply pressure in order to connect the electronic device interface (110) to an electronic device.

The electronic device interface (110) may include any number of electrical contact points (125) that may interface with an input/output port of an electronic device. In one example, the electronic device interface (110) is a universal serial bus (USB) interface capable of electrically coupling to a USB port in an electronic device. In other examples, the electrical contact points of the electronic device interface (110) may be configured to fit into a PCI bus, a PCIE bus, a SAS bus, and a SATA bus, among others. In still other examples, the electronic device interface (110) may include electrical contact points that interface with a specialized port in a specialized computing device.

The MDC (100) may include a feed tray (115) into which a fluid including an analyte and/or reactant is placed. The feed tray (115) directs the fluid into a fluidic slot (120) of the MDC (100). During operation, a fluid including an analyte, for example, may be placed in the feed tray (115) and passed into the fluidic slot (120). Although FIG. 1 shows a single feed tray (115) and a single fluidic slot (120), any plurality of feed trays (115) and fluidic slots (120) may be used in order to analyze a number of fluids.

When the fluid is in the fluidic slot (120) the MDC (100) may receive electrical power from an electrical device via the electronic device interface (110). The electrical power received from the electrical device may drive a number of pumps, sensors, and heaters within a number of microfluidic channels defined in the MDC (100).

The sensors of the MDC (100) may be impedance sensors capable of measuring an impedance value of a fluid as the fluid is passed over the sensor. In one example, the sensors may measure the number of particles within the fluid. As will be described in more detail below, a sensor may be placed in a secondary microfluidic channel branching away from a main microfluidic channel, which may have a relatively larger cross-sectional volume than the secondary microfluidic channel. Consequently, the secondary microfluidic channel may restrict particles within the fluid by size.

The pumps of the MDC (100) may pump the fluid through their respective microfluidic channels. The individual microfluidic channels may vary in width depending on the type of analysis to be conducted and the type of particles in the fluids (i.e., a specific analyte) used during the analysis. In one example, the width of the microfluidic channels may be slightly larger than the size of a single analyte particle such as a blood cell. In another example, the width of the microfluidic channels may be from 1-100 µm in diameter. In yet another example, the width of the microfluidic channels may be from 6-20 µm.

The pumps are resistors that, when a voltage is applied to them, nucleate a bubble at the surface of the thin film in contact with the fluid. This rapid Joule heating method superheats the fluid in intimate contact with a thin film resistor. The bubble formation and collapse causes the fluid to be pushed/pulled through the microfluidic channels. The thin film resistor may be made of, for example, tantalum, platinum, gold, silicon carbide, silicon nitride, tungsten, or combinations thereof. In one example, the voltage applied may be applied at a rate of 1-100 kHz and may range from 5-35V. In other examples, the voltage may be greater that 35V or less than 5V and may be applied at different frequencies. The frequency at which the resistor is activated in this manner may dictate the speed the fluid flows through the mains and secondary microfluidic channels. Additionally, as will be described in more detail below, the pumps may be cooperatively actuated in order to either push or pull the fluid and particles through different diameters of microfluidic channels.

Figure 2A:
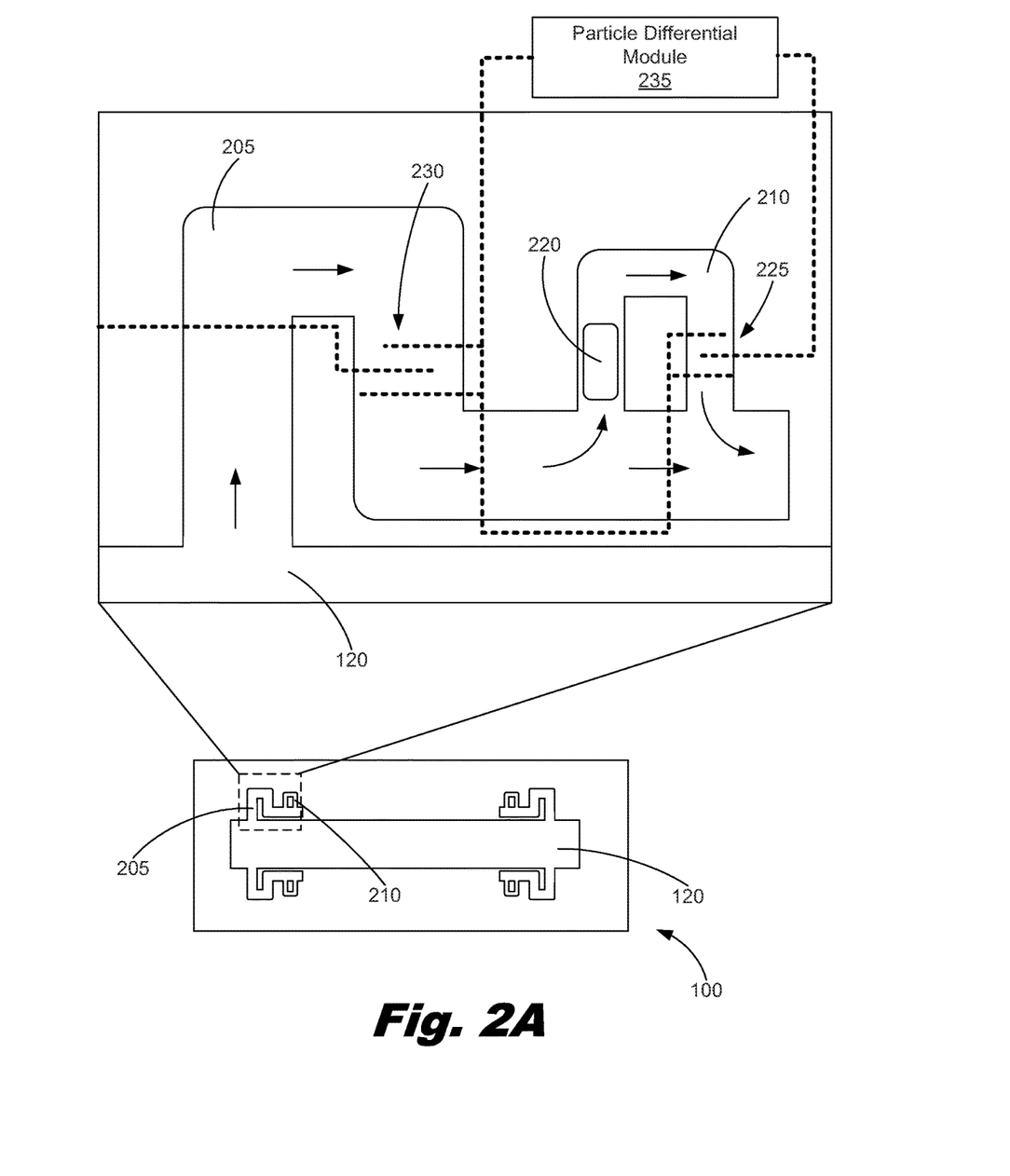
FIGS. 2A and 2B is a plan view diagram of a microfluidic diagnostic chip for separating particles within a fluid according to two examples of the principles described herein.
Figure 2B:
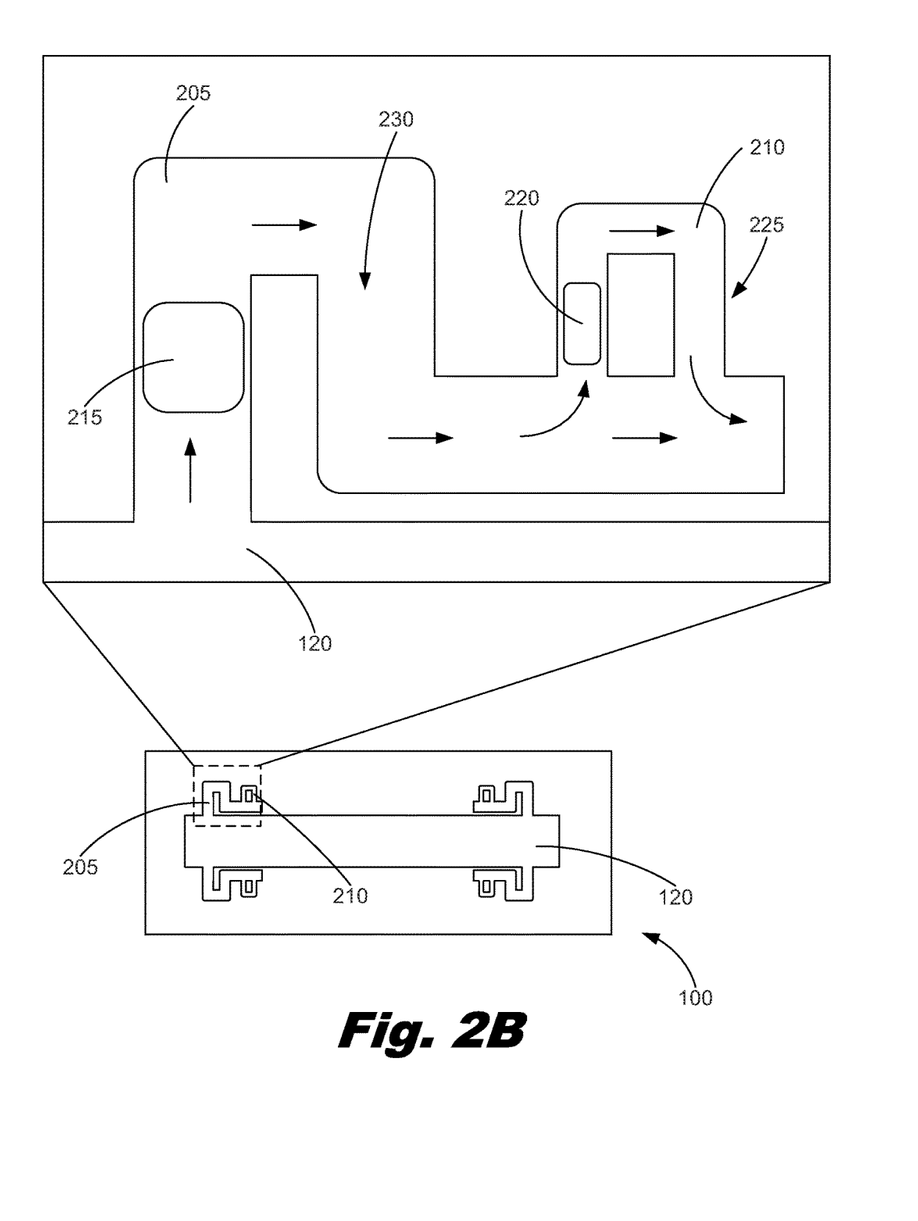

FIG. 2A is a plan view diagram of a microfluidic diagnostic chip (MDC) (100) for separating particles within a fluid according to one example of the principles described herein. FIG. 2B is a plan view diagram of a microfluidic diagnostic chip (MDC) (100) for separating particles within a fluid according to another example of the principles described herein. The MDC (100) will now be described with reference to these two figures. The MDC (100) may comprise a fluidic slot (120), a main channel (205), a secondary channel (210), a main channel pump (215), a secondary channel pump (220), and a secondary channel sensor (225). The fluidic slot (120) is a trough into which a fluid comprising an analyte is directed to via the feed tray (FIG. 1, 115). As the fluidic slot (120) fills up with the fluid, the fluid is received into a number of main channels (205). Both fluidic slot (120) and main channel (205) may be on the micrometer scale. In one example, the main channel (205) may be fluidly coupled to the fluidic slot (120) at the top of the fluidic slot (120) such that the entire fluidic slot (120) is to be full before the fluid passes into the main channel (205). In another example, the main channel (205) may be fluidly coupled to the fluidic slot (120) at the bottom of the fluidic slot (120) such that the fluid may immediately enter the main channel (205) once the fluid enters the fluid slot (120).

The main channel (205) may comprise a main channel pump (FIG. 2B, 215). As described above, the main channel pump (215) may be in the form of a resistor that nucleates a bubble within the fluid when a voltage is applied thereto. This superheats the fluid in intimate contact with a thin film resistor. The bubble then collapses causing the fluid to be pumped through the main fluidic channel in the direction indicated by the arrows show in FIGS. 2A and 2B.

The MDC (100) may further comprise a secondary channel (210) that branches away from the main channel (205). In one example, the terminal end of the secondary channel (210) is coupled to a discharge reservoir such that any particles within the fluid that have been directed into the secondary channel (210) are ejected from the MDC (100) and retained in the reservoir as a waste product of the analysis. In another example, the terminal end of the secondary channel (210) is redirected into the main channel (205) such that those particles in the fluid directed through the secondary channel (210) rejoin the fluid passing through the main channel (205). In this example, all particles passing through the main channel (210) may once again be analyzed by a sensor downstream of the secondary channel (210) and then disposed of by directing them into a reservoir.

The secondary channel (210) may further comprise a secondary channel sensor (225) that measures the characteristics of the particles in the fluid as they pass through the secondary channel (210). In one example, the sensor (225) may be an impedance sensor (225) that detects the presence of a particle such as a blood cell and counts how many of those particles pass through the secondary channel (210). Each secondary channel sensor (225) may comprise a number of electrical connections to receive power from a power source and to direct electrical signals to the electrical contact points (125) of the electronic device interface (110). FIG. 2 shows these electrical connections in dashed lines.

The secondary channel (220) has a cross-section volume smaller than that of the cross-sectional volume of the main channel (205). This allows fluid comprising particles of varying diameters to fit through the smaller secondary channel (220) while excluding larger particles. In one example, the fluid is a blood sample that comprises a number of different types of blood cells; each blood cell type having a different size diameter. In one example, the width of the secondary channel (220) may be slightly larger (i.e. tenths of a micrometer) than a target type of blood cell or particle to be analyzed.

In order to separate the different sizes of particles present in the fluid, the main channel pump (215) and the secondary channel pump (220) may cooperatively push and pull the individual cells through the main and secondary channels (205, 210) respectively. In one example, the main channel pump (215) may be situated and formed in the main channel (205) such that the fluid flows in the direction as indicated by the arrows shown in FIGS. 2A and 2B. The secondary channel pump (220) may be situated such that the target cells to be drawn into the secondary channel (210) are pulled into the secondary channel (210) by the secondary channel pump (220). In one example, activation of the main channel pump (215) and secondary channel pump (220) alternates with one pump (215, 220) activated while the other pump (215, 220) is deactivated. This alternating pattern of activation between the main channel pump (215) and secondary channel pump (220) provides for a cross flow to be created at the location where the secondary channel (210) branches away from the main channel (205). This prevents larger particles within the fluid from gathering by the entrance to the secondary channel (210) thereby preventing the intended particles from entering the secondary channel (210).

In one example, any number of particle excluding channels similar to the secondary channel (210) may branch away from the main channel (205) with each particle excluding channel having a different cross-sectional volume to exclude different sizes of particles from the fluid passing through the main channel (205). In this example, the number of particle excluding channels may be arranged such that the smaller of the number of particle excluding channels is upstream of any other particle excluding channel; each particle excluding channel increasing in cross-sectional volume the further the fluid passes downstream. Consequently, the smallest of particles present in the fluid is removed from the fluid before a relatively larger particle is removed by a relatively larger particle excluding channel. Each of the number of particle excluding channels may include a sensor thereby allowing each type of particle within the fluid to be detected and, in some examples, counted. As a consequence, the MDC (100) of the present specification may conduct multiple tests using a single fluid with many analytes deposited into the MDC (100). Additionally, the types of data received from the analysis may be used to make any number of diagnoses or conclusions.

Having the ability to sense many analytes within a fluid in secondary channels based on the size of the analyte allows for a relatively more accurate and precise particle count. In the example where the analyte is a cell type within the blood, a proper count of a certain type of cell found in the blood may help to better diagnose illnesses such as cancer, HIV, the flue, among others. The accuracy and precision is achieved by passing only one type of a target cell over the sensor within a channel specifically sized for that target cell (225). Without the pumps (215, 220) directing the target cells into the secondary channel (210), all types of cells may be passed across the sensor within the main channel having a diameter allowing multiple cells to pass simultaneously (225), which may cause a false read of inductance and thus a miscount on the number of target cells within the blood sample. In one example, a comparison may be made between the number of target cells detected by the secondary channel sensor (225) and the number of cells detected by a main channel sensor (230) using a particle differential module (235) communicatively coupled to the sensors (225, 230). In one example, the particle differential module (235) may be implemented as a computer readable medium having computer readable instructions thereon to, when executed by a processor, compare the difference between the output of the sensor (225) in the secondary channel (210) to the output of the sensor (230) in the main channel (205). In another example, the particle differential module (235) may be hardware circuitry that compares the difference between the output of the sensor (225) in the secondary channel (210) to the output of the sensor (230) in the main channel (205).

The comparison by the particle differential module (235) may be made so as to determine whether a relatively high target cell count or relatively low target cell count are present in the blood sample. Additionally, this comparison may be made across a number of particle excluding channels as described above, contributing even further to the accuracy and precision of the analysis conducted.

The present MDC (100) reduces the skill set necessary to conduct an analysis. A patient, for example, may provide his or her own fluid to a healthcare worker who may then place the fluid in the MDC (100) for analysis. In another example, a patient may also place his or her own fluid directly in the MDC (100). Through the electronic device interface (110) and computing device, results may be relayed to the healthcare worker for a diagnosis based on those results. Because a relatively higher skilled healthcare technician is not used, the cost of deploying the MDC (100) and conducting the test is significantly reduced. Further, the size of the main and secondary channels (205, 210) allows for the analysis of the blood sample on the microfluidic scale also contributing to the accuracy of the results and diagnosis.

Although the present specification describes the analyte as being a blood sample or elements therein, any type of fluid comprising a target particle may be passed through the MDC (100) without going beyond the present specification. Consequently, describing the analyte as a blood sample is merely an example and the present specification contemplates the use of the MDC (100) described herein to analyze a number of different particulates or analytes within a number of different fluids.

Figure 3:
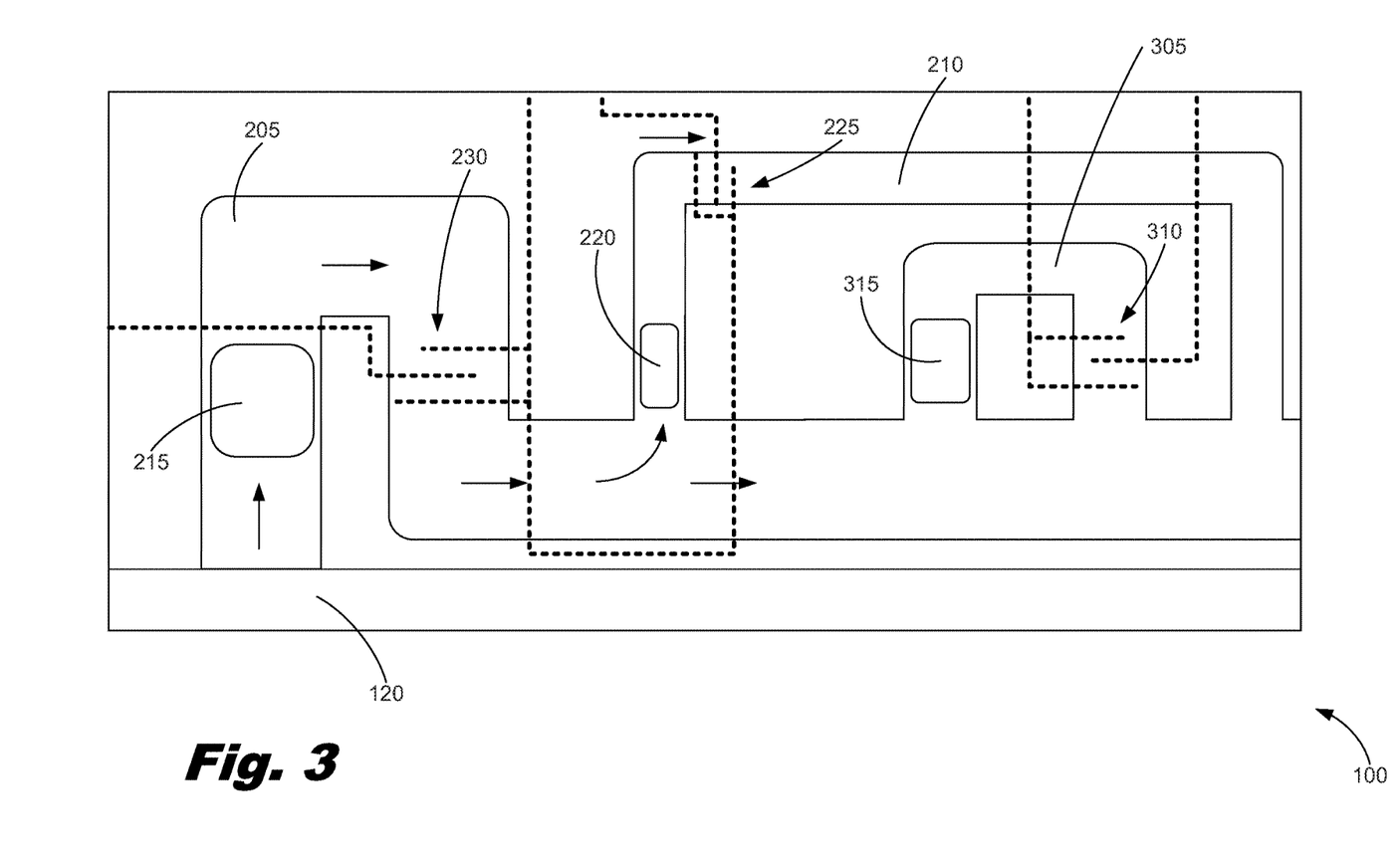
FIG. 3 is a plan view diagram of a microfluidic diagnostic chip for separating particles within a fluid according to another example of the principles described herein.

FIG. 3 is a plan view diagram of a microfluidic diagnostic chip (100) for separating particles within a fluid according to another example of the principles described herein. FIG. 3 is similar to FIGS. 2A and 2B except that FIG. 3 includes another tertiary channel (305) downstream of the secondary channel (210). The tertiary channel (305) may include a tertiary channel sensor (310) similar to the secondary channel sensor (225). The tertiary channel (305), however, may comprise a relatively larger width than the secondary channel (210) but a smaller width than the main channel (205). The operation of the MDC (100) shown in FIG. 3 is similar to the operation of the MDC (100) described in connection with FIGS. 2A and 2B. In FIG. 3, however, a second type of particle in the fluid passed through the main channel (205) may be analyzed by the tertiary channel sensor (310). The second type of particle may be those particles that do not include any other particles except those particles that can fit through the tertiary channel (305). In FIG. 3, because the secondary channel (210) bypasses the tertiary channel (305), all of a first type of particle pulled into the secondary channel (210) by the secondary channel pump (220) will not be pulled into the tertiary channel (305). Much like the secondary channel pump (220), the tertiary channel pump (315) located within the tertiary channel (305) pulls a second type of particle from the fluid in the main channel. Additionally, the tertiary channel pump (315) may cooperate with the secondary and main pumps (215, 220) to create a cross flow over the entrance to the tertiary channel (305). In this example, each pump (215, 220, 315) may fire sequentially one after the other.

As described above, any number of particle excluding channels similar to the secondary channel (210) and tertiary channel (305) may be used to, size by size, remove varying sizes of particles from the fluid in the main channel (205). Additionally, the data obtained by all the sensors may be compared to each other or compiled in a number of ways using the particle differential module (FIG. 2A, 235) and multiple diagnoses may be made as a result.

Figure 4:
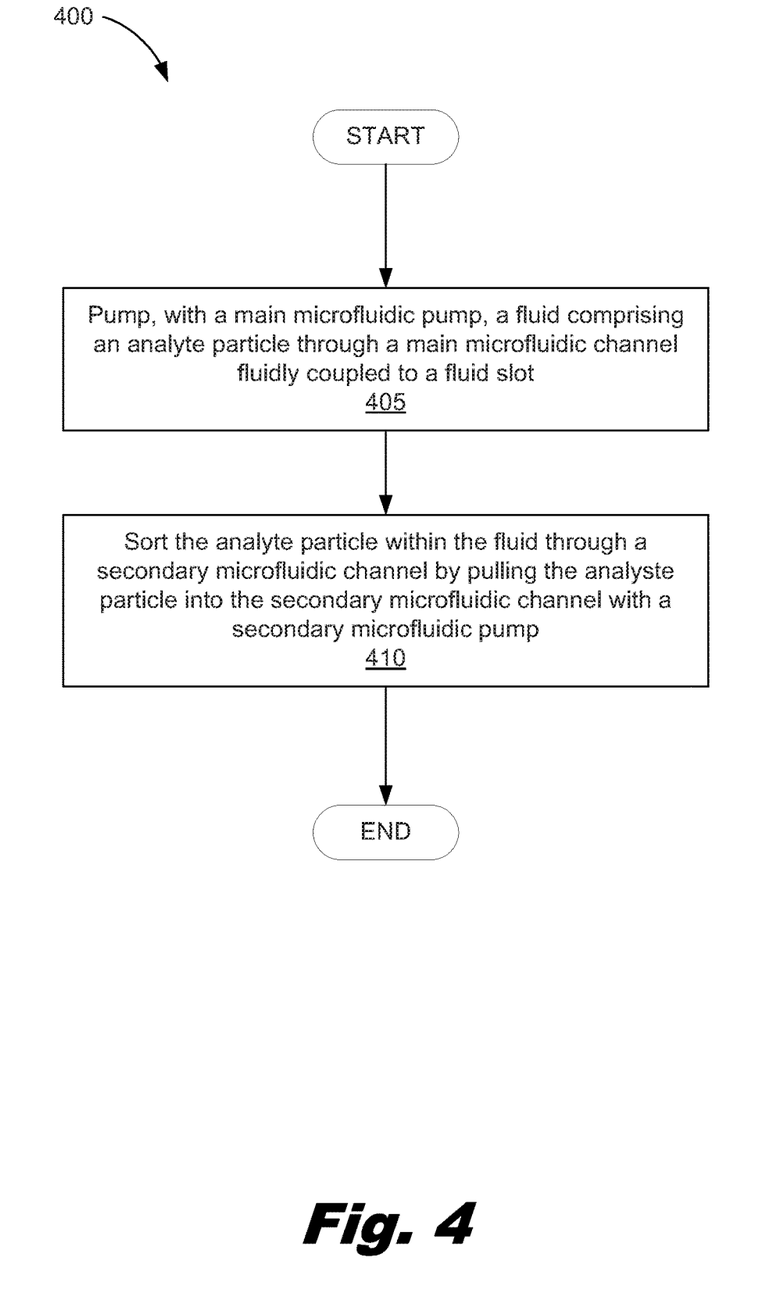
FIG. 4 is a flowchart showing a method of analyzing an analyte on a microfluidic diagnostic chip according to one example of the principles described herein.

FIG. 4 is a flowchart showing a method (400) of analyzing an analyte on a MDC according to one example of the principles described herein. The method may begin with pumping (405), with a main microfluidic pump, a fluid comprising an analyte particle through a main microfluidic channel (205) fluidly coupled to a fluid slot. As described above the main channel pump (215) may push an amount of the fluid through the main channel (205) using a resistor as described above.

The method (400) may continue with sorting (410) the particle within the analytic through a secondary microfluidic channel (210) by pulling the particle into the secondary microfluidic channel (210) with a secondary microfluidic pump (220). Similar to the main microfluidic pump (215), the secondary microfluidic pump (220) may also be a resistor. In this case, however, the nucleation and collapse of the bubble causes an amount of fluid and, where present, at least one particle in the fluid to be pulled into the secondary microfluidic channel (210). The two pumps (215, 220) work together to push and pull, respectively, at least one particle into the secondary microfluidic channel (210). In one example, a particle within the fluid may not be present to be pulled into the secondary microfluidic channel (210) with every activation of the pump (215, 220). When present, however, particles approaching the entrance of the secondary microfluidic channel (210) will be pulled into the secondary microfluidic channel (210).

Figure 5:
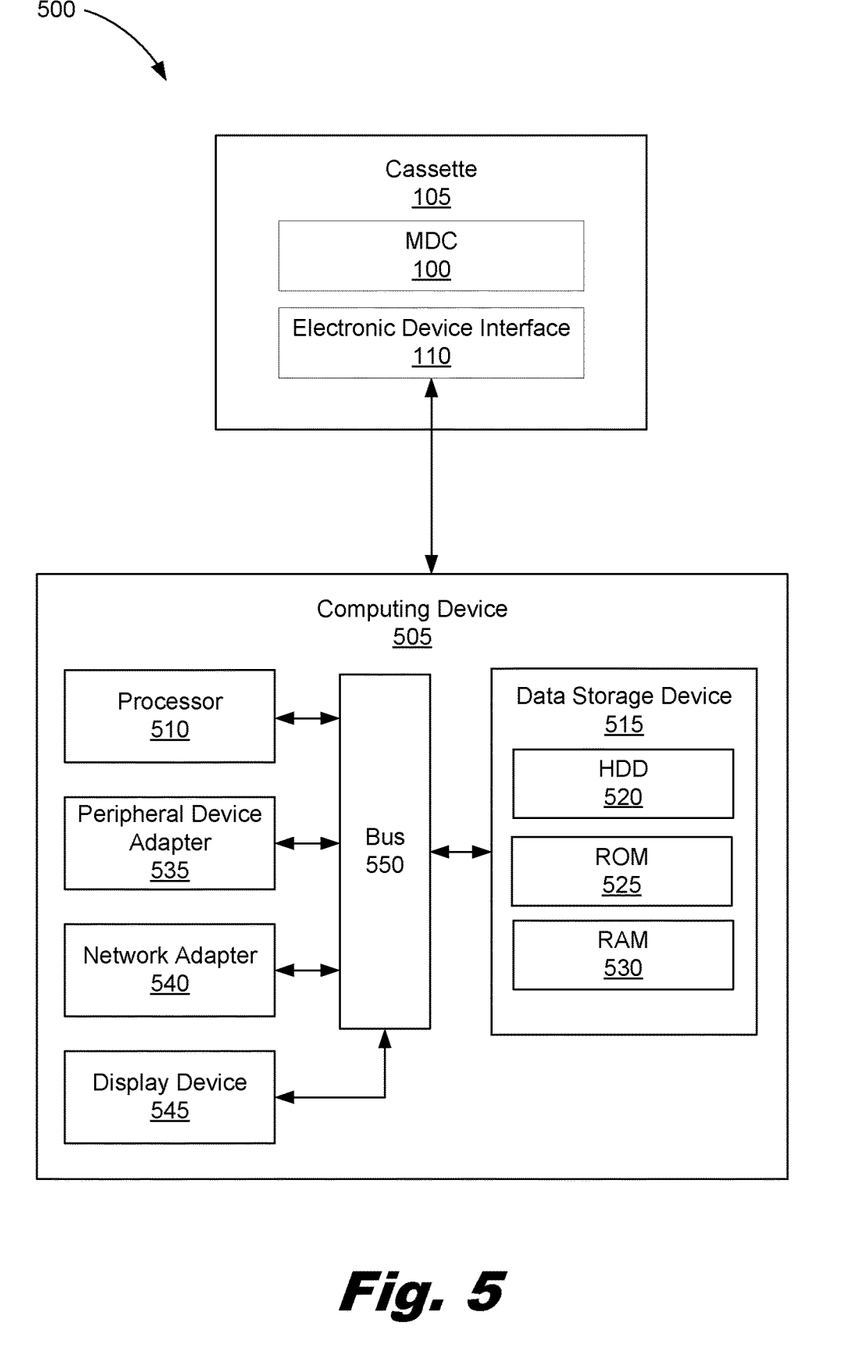
FIG. 5 is a block diagram of a microfluidic diagnostic chip system according to one example of the principles described herein. Throughout the drawings, identical reference numbers designate similar, but not necessarily identical, elements.

FIG. 5 is a block diagram of a microfluidic diagnostic chip system (500) according to one example of the principles described herein. The system (500) includes a computing device (505) and a cassette (105) selectively electrically coupled to the computing device (505). The cassette (105) includes a MDC (100) and an electronic device interface (110) as described above in connection with FIG. 1. In one example, the cassette (105) may be communicatively coupled to the computing device (505) via a USB connector.

The computing device (505) includes various hardware components. Among these hardware components may be a number of processors (510), a number of data storage devices (515), a number of peripheral device adapters (535), a number of network adapters (540), and a display device (545). These hardware components may be interconnected through the use of a number of busses (550) and/or network connections. In one example, the processor (510), data storage device (515), peripheral device adapters (535), network adapter (540), and display device (545) may be communicatively coupled via a bus (550).

The processor (510) may include the hardware architecture to retrieve executable code from the data storage device (515) and execute the executable code. The executable code may, when executed by the processor (510), cause the processor (510) to implement at least the functionality of receiving a number of electrical signals from the MDC (100) via the electronic device interface (110) and the peripheral device adapter (535), according to the methods of the present specification described herein. In the course of executing code, the processor (510) may receive input from and provide output to a number of the remaining hardware units.

The data storage device (515) may store data such as executable program code that is executed by the processor (510) or other processing device. As will be discussed, the data storage device (510) may specifically store computer code representing a number of applications that the processor (510) executes to implement at least the functionality described herein.

The data storage device (515) may include various types of memory modules, including volatile and nonvolatile memory. For example, the data storage device (515) of the present example includes Random Access Memory (RAM) (530), Read Only Memory (ROM) (525), and Hard Disk Drive (HDD) memory (520). Many other types of memory may also be utilized, and the present specification contemplates the use of many varying type(s) of memory in the data storage device (515) as may suit a particular application of the principles described herein. In certain examples, different types of memory in the data storage device (515) may be used for different data storage needs. For example, in certain examples the processor (510) may boot from Read Only Memory (ROM) (525), maintain nonvolatile storage in the Hard Disk Drive (HDD) memory (520), and execute program code stored in Random Access Memory (RAM) (530).

Generally, the data storage device (515) may comprise a computer readable medium, a computer readable storage medium, or a non-transitory computer readable medium, among others. For example, the data storage device (515) may be, but not limited to, an electronic, magnetic, optical, electromagnetic, infrared, or semiconductor system, apparatus, or device, or any suitable combination of the foregoing. More specific examples of the computer readable storage medium may include, for example, the following: an electrical connection having a number of wires, a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. In the context of this document, a computer readable storage medium may be any tangible medium that can contain, or store computer usable program code for use by or in connection with an instruction execution system, apparatus, or device. In another example, a computer readable storage medium may be any non-transitory medium that can contain, or store a program for use by or in connection with an instruction execution system, apparatus, or device.

The hardware adapters (535, 540) in the computing device (505) enable the processor (510) to interface with various other hardware elements, external and internal to the computing device (510). For example, the peripheral device adapters (535) may provide an interface to input/output devices, such as, for example, display device (545), a mouse, or a keyboard. The peripheral device adapters (535) may also provide access to other external devices such as an external storage device, a number of network devices such as, for example, servers, switches, and routers, client devices, other types of computing devices, and combinations thereof.

The display device (545) may be provided to allow a user of the computing device (545) to interact with and implement the functionality of the computing device (545). The peripheral device adapters (535) may also create an interface between the processor (510) and the display device (545), a printer, or other media output devices. The network adapter (540) may provide an interface to other computing devices within, for example, a network, thereby enabling the transmission of data between the computing device (545) and other devices located within the network.

Aspects of the present system and method are described herein with reference to flowchart illustrations and/or block diagrams of methods, apparatus (systems) and computer program products according to examples of the principles described herein. Each block of the flowchart illustrations and block diagrams, and combinations of blocks in the flowchart illustrations and block diagrams, may be implemented by computer usable program code. The computer usable program code may be provided to a processor of a general purpose computer, special purpose computer, or other programmable data processing apparatus to produce a machine, such that the computer usable program code, when executed via, for example, the processor (510) of the computing device (505) or other programmable data processing apparatus, implement the functions or acts specified in the flowchart and/or block diagram block or blocks. In one example, the computer usable program code may be embodied within a computer readable storage medium; the computer readable storage medium being part of the computer program product. In one example, the computer readable storage medium is a non-transitory computer readable medium.

The specification and figures describe a diagnostic chip that may separate particles from a fluid. This diagnostic chip may, in some examples, reduce the skill set requirements for a healthcare worker conducting an analysis. The MDC (100) described herein may, in some examples, allow a nonprofessional to place an analyte into the MDC (100) and retrieve analytical data of that analyte. Consequently, the cost of deploying the MDC (100) may, in some examples, be relatively cheaper than spending potentially thousands of dollars paying a professional to analyze an analyte in a professional lab. Additionally, the size of the components in the MDC (100) may, in some examples, allow the analyte to be analyzed on the micron level providing better precision and accuracy in the analysis with relatively smaller amounts of the fluid sample.

The preceding description has been presented to illustrate and describe examples of the principles described. This description is not intended to be exhaustive or to limit these principles to any precise form disclosed. Many modifications and variations are possible in light of the above teaching.

What is claimed is:

1. A microfluidic diagnostic chip, comprising:
   a main fluid channel comprising a main pump;
   a secondary fluid channel branching off from the main fluid channel;
   a secondary pump within the secondary fluid channel wherein the secondary pump is to pull a particle of analyte of a first size from a fluid passing through the main channel, the fluid comprising particles of analyte of the first size and of a number of larger sizes; and
   a particle differential module to compare an output of a first sensor in the secondary fluid channel with an output of a second sensor in the main fluid channel.

2. The microfluidic diagnostic chip of claim 1, wherein the secondary fluid channel comprises a smaller diameter than the main fluid channel.

3. The microfluidic diagnostic chip of claim 2, wherein the first sensor is to count a number of the particles of the first size passing through the secondary fluid channel.

4. The microfluidic diagnostic chip of claim 2, wherein the diameter of the secondary fluid channel excludes the number of larger sizes of particles.

5. The microfluidic diagnostic chip of claim 3, wherein the second sensor is to count particles of the analyte of the first size and larger sizes passing through the main fluid channel.

6. The microfluidic diagnostic chip of claim 5, wherein the particle differential module is to receive the detected number of the first size of particle and the detected number of particles of larger sizes and compare the number of the particles of the first size to the particles of larger sizes within the fluid.

7. The microfluidic diagnostic chip of claim 1, wherein the main pump and secondary pump are to cooperate to push and pull, respectively, the particle of the first size into the secondary fluid channel.

8. The microfluidic diagnostic chip of claim 1, further comprising an ejection mechanism downstream of the secondary fluid channel to eject the particle of the first size through a nozzle and out of the microfluidic diagnostic chip.

9. The diagnostic chip of claim 1, wherein
   the first sensor is to be communicatively coupled to the particle differential module;
   second sensor is to be communicatively coupled to the particle differential module; and
   the particle differential module is to compare a number of analyte particles that have passed through the main fluid channel to a number of analyte particles that have that have been pulled through the secondary fluid channel using the secondary pump.

10. The diagnostic chip of claim 1, wherein the main and secondary pumps cooperate to create a cross flow of fluid by an opening of the secondary fluid channel such that particles in the fluid do not accumulate at the opening.

11. The diagnostic chip of claim 1, wherein the first and second sensors are impedance sensors.

12. A method of operating the microfluidic diagnostic chip of claim 1 for analyzing an analyte, the method comprising:
   pumping, with the main pump, a fluid comprising an analyte particle through the main fluid channel fluidly coupled to a fluid slot; and
   sorting the analyte particle within the fluid through the secondary fluid channel by pulling the analyte particle into the secondary fluid channel with the secondary pump.

13. The method of claim 12, wherein a count of the number of analyte particles passed through the secondary fluid channel are compared to a count of number of total particles within the fluid passed through the main fluid channel using a main microfluidic sensor.

14. The microfluidic diagnostic chip of claim 1, wherein the microfluidic diagnostic chip is housed within a cassette.

15. The microfluidic diagnostic chip of claim 1, further comprising a fluidic slot coupled to multiple main fluid channels.

16. The microfluidic diagnostic chip of claim 15, wherein:
   a first main channel is fluidly coupled at a top of the fluidic slot such that the fluidic slot is full before fluid passes into the first main channel; and
   a second main channel is fluidly coupled at a bottom of the fluidic slot such that the fluid enters the second main channel once fluid enters the fluid slot.

17. The microfluidic diagnostic chip of claim 1, wherein a terminal end of the secondary fluid channel is coupled to a discharge reservoir.

18. The microfluidic diagnostic chip of claim 1, wherein the main pump and the secondary pump alternate activation with one another.

19. The microfluidic diagnostic chip of claim 1, further comprising a tertiary fluid channel.

20. The microfluidic diagnostic chip of claim 19, wherein the secondary fluid channel bypasses the tertiary fluid channel.

* * * * *

UNITED STATES PATENT AND TRADEMARK OFFICE
CERTIFICATE OF CORRECTION

PATENT NO. : 10,464,066 B2
APPLICATION NO. : 15/546565
DATED : November 5, 2019
INVENTOR(S) : Nicholas McGuinness et al.

Page 1 of 1

It is certified that error appears in the above-identified patent and that said Letters Patent is hereby corrected as shown below:

In the Drawings

In sheet 5 of 6, Fig. 4, reference numeral 410, Line 2, delete "analyste" and insert -- analyte --, therefor.

In the Claims

In Column 10, Line 62, Claim 9, after "have" delete "that have".

Signed and Sealed this
Third Day of March, 2020

Andrei Iancu
*Director of the United States Patent and Trademark Office*